United States Patent
Jacobs et al.

(10) Patent No.: US 10,842,835 B2
(45) Date of Patent: Nov. 24, 2020

(54) ONCOLYTIC VACCINIA VIRUS MUTANTS AND USING SAME FOR CANCER TREATMENT

(71) Applicant: ARIZONA BOARD OF REGENTS ON BEHALF OF ARIZONA STATE UNIVERSITY, Scottsdale, AZ (US)

(72) Inventors: Bertram Jacobs, Tempe, AZ (US); Heather Koehler, Phoenix, AZ (US); William Arndt, Albuquerque, NM (US); Karen Kibler, Scottsdale, AZ (US); Kelly Trainor, Prescott, AZ (US); Chandra Mitnik, Tempe, AZ (US); Jeffrey Langland, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 16/304,564

(22) PCT Filed: May 25, 2017

(86) PCT No.: PCT/US2017/034552
§ 371 (c)(1),
(2) Date: Nov. 26, 2018

(87) PCT Pub. No.: WO2017/205674
PCT Pub. Date: Nov. 30, 2017

(65) Prior Publication Data
US 2019/0183947 A1 Jun. 20, 2019

Related U.S. Application Data

(60) Provisional application No. 62/341,450, filed on May 25, 2016.

(51) Int. Cl.
| | | |
|---|---|---|
| *A61K 35/768* | (2015.01) | |
| *C12N 7/00* | (2006.01) | |
| *A61P 35/00* | (2006.01) | |
| *A61K 9/00* | (2006.01) | |
| *A61K 45/06* | (2006.01) | |

(52) U.S. Cl.
CPC .......... *A61K 35/768* (2013.01); *A61K 9/0019* (2013.01); *A61P 35/00* (2018.01); *C12N 7/00* (2013.01); *A61K 45/06* (2013.01); *C12N 2710/24121* (2013.01); *C12N 2710/24122* (2013.01); *C12N 2710/24132* (2013.01)

(58) Field of Classification Search
None
See application file for complete search history.

(56) References Cited

U.S. PATENT DOCUMENTS

| | | |
|---|---|---|
| 5,762,938 A | 6/1998 | Paoletti et al. |
| 2002/0028195 A1 | 3/2002 | Coffey et al. |
| 2002/0155529 A1 | 10/2002 | Jacobs et al. |
| 2003/0044384 A1 | 3/2003 | Roberts et al. |
| 2005/0028226 A1 | 2/2005 | Erfle et al. |
| 2006/0008470 A1 | 1/2006 | Jacobs et al. |
| 2007/0036758 A1* | 2/2007 | Jacobs ................ C07K 14/005 424/93.2 |
| 2010/0203147 A1 | 8/2010 | Coffey et al. |
| 2010/0303714 A1* | 12/2010 | Kirn ...................... C12N 15/86 424/1.11 |

FOREIGN PATENT DOCUMENTS

| | | |
|---|---|---|
| EP | 1648233 | 4/2006 |
| WO | 2000062735 A2 | 10/2000 |
| WO | 2000073487 A1 | 12/2000 |
| WO | 2001035970 A1 | 5/2001 |
| WO | 2004003562 A2 | 1/2004 |
| WO | 2005007824 A2 | 1/2005 |
| WO | 2017205674 A1 | 11/2017 |

OTHER PUBLICATIONS

Feng et al. Receptor-interacting protein kinase 3 is a predictor of survival and plays a tumor suppressive role in colorectal cancer. Neoplasma, 2015, 62:592-601.*
Lu et al. RIP3 overexpression sensitizes human breast cancer cells to parthenolide in vitro via intracellular ROS accumulationActa Pharmacologica Sinica (2014) 35: 929-936.*
Chang, H. et al., "Identification of a Conserved Motif That Is Necessary for Binding of the Vaccinia Virus E3L Gene Products to Double-Stranded RNA", Virology, Jun. 1993, 194(2), pp. 537-547.
Chang, H. et al., "Rescue of vaccinia virus lacking the E3L gene by mutants of E3L", Journal of Virology, Oct. 1995, 69(10), pp. 6605-6608.
Chang, H. et al., "The E3L gene of vaccinia virus encodes an inhibitor of the interferon-induced, double-stranded RNA-dependent protein kinase", PNAS, Jun. 1992, 89(11), pp. 4825-4829.
Cho, Y. et al., "Phosphorylation-Driven Assembly of RIP1-RIP3 Complex Regulates Programmed Necrosis and Virus-Induced Inflammation", Cell, Jun. 2009, 137(6), pp. 1112-1123.
European Patent Office, Communication Pursuant to Article 96(2) EPC for 04777944.2-2401, dated Feb. 16, 2007, 4 pages.
European Patent Office, Communication Pursuant to Article 96(3) EPC for 04777944.2-2401, dated Apr. 7, 2008, 4 pages.
European Patent Office, Supplementary European Search Report for 04777944.2-2103, dated Jul. 24, 2006, 5 pages.
Goebel, S. et al., "Appendix to "The complete DNA sequence of vaccinia virus"", Virology, 1990, 179(1), pp. 517-563.

(Continued)

*Primary Examiner* — Nianxiang Zou
(74) *Attorney, Agent, or Firm* — Quarles & Brady LLP

(57) ABSTRACT

Methods utilizing vaccinia virus with mutations in E3L to infect and cause lysis of cancer cells with less than normal protein levels of RIP3 and/or DAI. Further, the disclosed vaccinia viruses with mutations in E3L cannot replicate well in cells with normal expression or upregulation of RIP3, DAI, and/or MLKL.

12 Claims, 15 Drawing Sheets

Specification includes a Sequence Listing.

(56) References Cited

OTHER PUBLICATIONS

Goebel, S. et al., "The complete DNA sequence of vaccinia virus", Virology, 1990, 179(1), pp. 247-266.
Guo, H. et al., "Herpes simplex virus suppresses necroptosis in human cells", Cell Host & Microbe, Feb. 2015, 17(2), pp. 243-251.
Kaiser, W. et al., "Viral modulation of programmed necrosis", Current Opinion in Virology, Jun. 2013, 3(3), pp. 296-306.
Kim Y. et al., "A role for Z-DNA binding in vaccinia virus pathogenesis", PNAS, Jun. 2003 (published first May 2003), 100(12), pp. 6974-6979.
Koo, G. et al., "Methylation-dependent loss of RIP3 expression in cancer represses programmed necrosis in response to chemotherapeutics", Cell Research, May 2015, 25, pp. 707-725.
Langland et al., "The Role of the PKR-Inhibitory Genes, E3L and K3L, in Determining Vaccinia Virus Host Range", Virology, Jul. 2002, 299(1), pp. 133-141.
Lee et al., "The Interferon-induced double stranded RNA-activated protein kinase induces apoptosis", Virology, Mar. 1994, 199, pp. 491-496.
Morikawi, K. et al., "Differential roles of RIPK1 and RIPK3 in TNF-induced necroptosis and chemotherapeutic agent-induced cell death", Cell Death and Disease, Feb. 2015, 6, article e1636, 11 pages, doi:10.1038/cddis.2015.16.
Morikawi, K. et al., "RIP3: a molecular switch for necrosis and inflammation", Genes & Development, Aug. 2013, 27(15), pp. 1640-1649.
Omoto, S. et al., "Suppression of RIP3-dependent necroptosis by human cytomegalovirus", Journal of Biological Chemistry, May 2015 (first published Mar. 2015), 290(18), pp. 11635-11648.
Patent Cooperation Treaty, International Searching Authority, International Preliminary Report on Patentability and Written Opinion for PCT/US2004/022165, 4 pages, opinion dated Jan. 13, 2005, report dated Jan. 9, 2006.
Patent Cooperation Treaty, International Searching Authority, International Search Report for PCT/US2004/022165, 3 pages, dated Jan. 13, 2005.
Patent Cooperation Treaty, International Searching Authority, International Search Report for PCT/US2017/034552, 3 pages, dated Aug. 16, 2017.
Patent Cooperation Treaty, International Searching Authority,Written Opinion for PCT/US2017/034552, 6 pages, dated Aug. 16, 2017.
Piccini, A. et al., "Vaccinia Virus as an Expression Vector", Methods in Enzymology, 1987, 153, 545-563.
Romano, R. et al., "Inhibition of Double-Stranded RNA-Dependent Protein Kinase PKR by Vaccinia Virus E3: Role of Complex Formation and the E3 N-Terminal Domain", Molecular and Cellular Biology, Dec. 1998, 18(12), pp. 7304-7316.
Seymour, L. et al., "Oncolytic viruses: finally delivering", British Journal of Cancer, Jan. 2016, 114, pp. 357-361.
Sharp, T. et al., "The Vaccinia Virus E3L Gene Product Interacts with both the Regulatory and the Substrate Binding Regions of PKR: Implications for PKR Autoregulation", Virology, Oct. 1998, 250(2), pp. 302-315.
Shors, T. et al., Complementation of Vaccinia Virus Deleted of the E3L Gene by Mutants of E3L, Virology, Dec. 1997, 239(2), pp. 269-276.
Upton, J. et al., "DAI complexes with RIP3 to mediate virus-induced programmed necrosis that is targeted by murine cytomegalovirus vIRA", Cell Host & Microbe, Mar. 2012, 11(3), pp. 290-297.
USPTO, Non-Final Rejection for U.S. Appl. No. 10/563,728, dated Jul. 6, 2007, 10 pages.
USPTO, Non-Final Rejection for U.S. Appl. No. 10/563,728, dated Nov. 19, 2007, 12 pages.
USPTO, Non-Final Rejection for U.S. Appl. No. 10/563,728, dated Jun. 13, 2008, 9 pages.
Whilding, L. et al., "Vaccinia virus induces programmed necrosis in ovarian cancer cells", Molecular Therapy, Nov. 2013 (advance online publication Sep. 2013), 21(11), pp. 2074-2086.
White, S. et al., "The amino terminus of the vaccinia virus E3 protein is necessary to inhibit the interferon response", Journal of Virology, May 2012 (published online Apr. 2012), 86(10), pp. 5895-5904.
Earl, P. et al., "Vaccinia Virus", in Genetic maps: locus maps of complex genomes (ed. O'Brien), 1993, Cold Spring Harbor Laboratory Press, Cold Spring Harbor, NY, pp. 1.157-1.165.

* cited by examiner

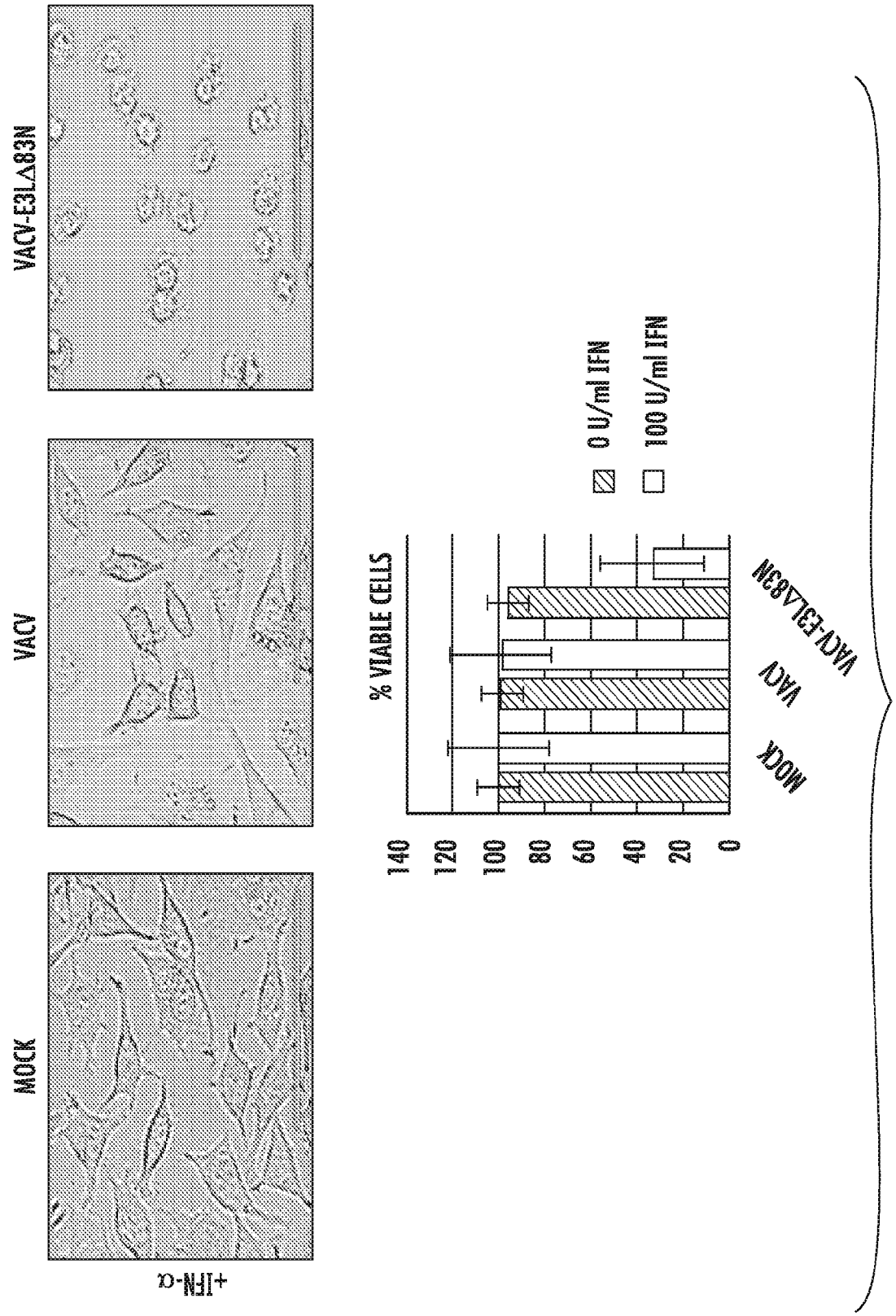

SYNGENEIC MODEL

- TUMOR TREATMENT: PBS
- INJECTED TUMOR (RIGHT SIDE)

TUMOR TREATMENT: VACV-E3LΔ83N @ 1x10⁷ pfu

UNINJECTED TUMOR (LEFT SIDE)

INJECTED TUMOR (RIGHT SIDE)

SEQUENCE LISTING

```
<160> NUMBER OF SEQ ID NOS: 2

<210> SEQ ID NO 1
<211> LENGTH: 333
<212> TYPE: DNA
<213> ORGANISM: Vaccinia virus

<400> SEQUENCE: 1
atgggcccca taatagatga tgtatcccgc gaaaaatcaa tgagagagga tcataagtct      60
tttgatgatg ttattccggc taaaaaaatt attgattgga aaggtgctaa ccctgtcacc     120
gttattaatg agtactgcca aattactagg agagattggt cttttcgtat tgaatcagtg     180
gggcctagta actctcctac attttatgcc tgtgtagaca tcgacggaag agtattcgat     240
aaggcagatg gaaaatctaa acgagatgct aaaaataatg cagctaaatt ggcagtagat     300
aaacttcttg gttacgtcat cattagattc tga                                  333

<210> SEQ ID NO 2
<211> LENGTH: 411
<212> TYPE: DNA
<213> ORGANISM: Vaccinia virus

<400> SEQUENCE: 2
atggtgtaca gctccgacga tattcctcct cgttggttta tgacaacgga ggcggataag      60
ccggatgctg atgctatggc tgacgtcata atagatgatg tatcccgcga aaaatcaatg     120
agagaggatc ataagtcttt tgatgatgtt attccggcta aaaaattat tgattggaaa     180 gatgctaacc ctgtcaccat tattaatgag tactgccaaa taactaagag agattggtct     240
tttcgtattg aatcagttgg gcctagtaac tctcctacat tttatgcctg tgtagacatc     300
gacggaagag tattcgataa ggcagatgga aaatctaaac gagatgctaa aaataatgca     360
gctaaattgg cagtagataa acttcttggt tacgtcatca ttagattctg a              411
```

ONCOLYTIC VACCINIA VIRUS MUTANTS AND USING SAME FOR CANCER TREATMENT

CROSS-REFERENCE TO RELATED APPLICATIONS

This application represents the national stage entry of PCT International Application No. PCT/US2017/034552, filed on May 25, 2017, and claims priority to U.S. Provisional Patent Application No. 62/341,450 filed on May 25, 2016, the disclosures of which are incorporated herein by reference.

STATEMENT REGARDING FEDERALLY SPONSORED RESEARCH

This invention was made with government support under R01 AI095394 awarded by the National Institutes of Health. The government has certain rights in the invention.

BACKGROUND

Numerous advances have been made in cancer therapies. Despite the significant improvements in the field of oncology, the number of cancer-related deaths continues to rise. With annual increases in the number of cancer diagnoses, it is urgent to identify and develop new cancer therapies. The conventional therapies are generally effective initially but tumors continue to reoccur and/or become resistant to the initial therapies.

Oncolytic viruses are mutants of viruses that have been engineered to replicate in and destroy cancerous cells. Oncolytic viruses can be used to selectively infect and destroy cancerous cells, leaving the normal non-cancerous cell unharmed. This is possible because many tumors arise through genetic mutations that result in a loss of function in cellular proteins and signaling pathways such as the interferon (IFN) system. These mutations commonly result in a dysregulation of cellular anti-proliferative checkpoints, as well as defects in programmed cell death pathways, thereby allowing for unregulated cellular growth.

Vaccinia virus (VACV) is a member of the orthopoxvirus genus that contains a large double-stranded DNA (dsDNA) genome that encodes for numerous immune evasion proteins. The large dsDNA allows for manipulation of the virus to express tumor-specific antigens or to decrease any potential side effects associated with treatment.

SUMMARY

The present disclosure relates to mutant oncolytic vaccinia viruses and the use of such viruses alone and in combination with different chemotherapeutic agents for destruction of cancer cells.

Host organisms have evolved multiple mechanisms to defend against a viral infection and parallel viruses have evolved multiple methods to subvert the host's anti-viral immune response. VACV is known to contain numerous proteins involved in blocking the cellular anti-viral immune response. For example, the VACV E3L gene product is important for inhibiting the cellular anti-viral immune response. Thus, mutations within this gene lead to severe virus attenuation. However, vaccinia virus with such mutations can selectively replicate in and destroy cancerous cells while leaving normal cells unharmed.

The embodiments of the present disclosure describe a method of inducing lysis of cancer cells that are deficient in an ability to activate a programmed cell death pathway. The method comprises contacting said cancer cells with a vaccinia virus (VACV) having a mutation in an E3L gene of said virus, wherein said cancer cells have less than normal protein levels of one or more of a receptor-interacting protein kinase (RIP) 3, a DNA-dependent activator of interferon regulatory factor (DAI), and a lineage kinase domain-like protein (MLKL).

Moreover, embodiments are directed to a method of inducing oncolysis in a subject having a tumor, the method comprising administering to the subject a therapeutically effective amount of a pharmaceutical composition comprising a vaccinia virus (VACV) having a mutation in an E3L gene of said virus. Further, the method comprising administering to the subject at least one chemotherapeutic agent.

Furthermore, embodiments are directed to a pharmaceutical composition for treating a cancer, the composition comprising a vaccinia virus (VACV) having a mutation in an E3L gene of said virus and a pharmaceutically acceptable carrier. The composition further comprises at least one chemotherapeutic agent.

BRIEF DESCRIPTION OF THE DRAWINGS

FIGS. 2A-2D: Truncation of the N-terminus of E3 results in IFN sensitivity and leads to reduced plaquing efficiency, global protein loss, loss of membrane integrity and a rapid cell death which is atypical for classical apoptosis. (2A) Pretreatment for 18 hours with type-1 IFN resulted in a 50% reduction of plaquing efficiency of VACV with an N-terminal truncated E3 protein at a dose between 3 and 10 U/ml. (2B) Total cellular protein stained with coomassie blue demonstrates a global loss of protein in type-1 IFN treated cells which were subsequently infected with an E3 N-terminus truncated mutant. (2C) Live imaging of cells at 6 hours post infection (HPI) stained with Hoechst nuclear stain demonstrate a drastic reduction in membrane integrity and morphological changes. (2D) Sytox inclusion viability assay preformed on cells at 5 HPI demonstrates a significant reduction of viability that is specific to cells pretreated with type-1 IFN and infected with E3 N-terminal truncations.

DETAILED DESCRIPTION

Figure 1:
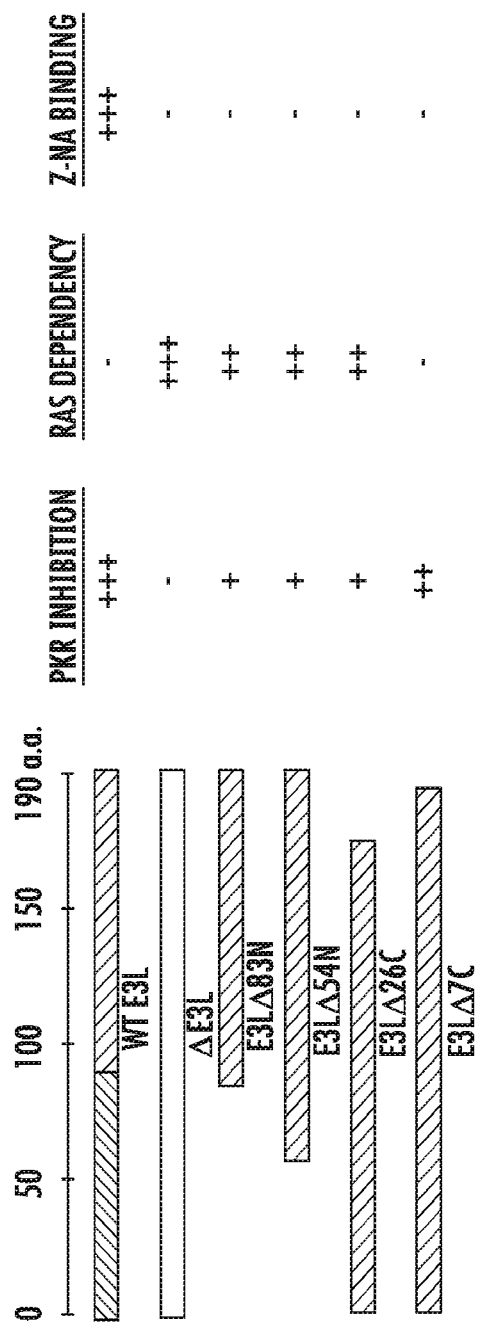
FIG. 1: The diagram describes deletion mutants of E3L in vaccinia virus and their PKR inhibitory, ras-dependency, and Z-NA binding characteristics.

This technology disclosed herein is described in one or more exemplary embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

Vaccinia viruses offer a promising alternative to current anti-cancer therapies, especially mutant vaccinia viruses that are interferon-sensitive. Other oncolytic viruses, including herpesvirus, adenovirus, and wild-type vaccinia virus constructs can still harm healthy cells. In certain embodiments, the Vaccinia viruses selectively kill cancer cells, leaving healthy cells unharmed. Further, the virus is able to infect cancer cells that have a disrupted programmed cell-death pathway necessary for a defense against viruses; without an intact programmed cell-death pathway, mutant viruses are able to replicate and spread in the cancer cells. However, these same mutant viruses are blocked from replicating in normal healthy cells, which have an intact anti-viral pathway.

Embodiments herein relate to the mutant oncolytic vaccinia viruses and the use of such viruses alone and in combination with different chemotherapeutic agents for destruction of cancer cells. The type I interferons (IFNs) are a group of related proteins that are produced and secreted by mammalian cells in response to various inducers, such as double-stranded (ds)RNA and viral infection. IFNs bind to specific receptors on cells and induce an antiviral state. Cells in the antiviral state are resistant to infection by many viruses. At least two IFN-induced enzymatic pathways are involved in establishment of the antiviral state. One of the IFN-induced enzymes is Protein kinase RNA-activated, also known as protein kinase R (PKR); interferon-induced, double-stranded RNA-activated protein kinase; or eukaryotic translation initiation factor 2-alpha kinase 2 (EIF2AK2) which is an enzyme that in humans is encoded by the EIF2AK2 gene. Once active, PKR is able to phosphorylate the eukaryotic translation initiation factor eIF-2α.

Phosphorylation of eIF-2 on its α subunit alters its interaction with eIF-2β, leading to inhibition of initiation of translation of viral genes. A number of viruses, including vaccinia virus have been shown to induce inhibitors of the P1/eIF-2α kinase. Vaccinia virus-infected mouse L cells are resistant to IFN treatment and the vaccinia virus inhibitor of the IFN-induced protein kinase is responsible for IFN resistance of vaccinia virus. The vaccinia virus kinase inhibitors p25 and p20, which are encoded by vaccinia virus open reading frame (ORF) E3L, has been reported to be a protein that interacts in a stoichiometric manner with dsRNA. The E3L gene products act as inhibitors of the dsRNA-dependent P1/eIF-2a kinase.

The receptor-interacting protein (RIP) kinase family members have emerged as essential sensors of intracellular and extracellular stresses. RIP kinases are a group of threonine/serine protein kinases with a relatively conserved kinase domain but distinct non-kinase regions. Programmed necrotic cell death induced by the tumor necrosis factor alpha (TNF-α) family of cytokines is dependent on a kinase cascade consisting of receptor-interacting kinases RIP1 and RIP3. RIP3 is comprised of an N-terminal kinase domain similar to that found in other RIP kinases, an RHIM domain and a unique C-terminal domain that differs from all known protein domains. Overexpression of RIPS could induce apoptosis and NF-κB activation in some cell lines. TNF-α induces apoptosis in many types of cells, which can be blocked by the pan caspase inhibitor benzyloxycarbonyl-Val-Ala-Asp(OMe)-fluoromethylketone (zVAD), but TNF-α can still trigger some cell lines to undergo necrosis when the activities of caspases are inhibited by zVAD treatment. The kinase activity of RIP3 is required for this caspase-independent cell death.

Further, the mixed lineage kinase domain-like protein MLKL is a functional RIP3 substrate that binds to RIP3 through its kinase-like domain but lacks kinase activity of its own. RIP3 phosphorylates MLKL at the T357 and S358 sites. The phosphorylated MLKL forms an oligomer that binds to phosphatidylinositol lipids and cardiolipin. This property allows MLKL to move from the cytosol to the plasma and intracellular membranes, where it directly disrupts membrane integrity, resulting in necrotic death.

Moreover, DNA-dependent activator of interferon-regulatory factors (DAI) functions as a cytoplasmic DNA sensor that activates the innate immune system and is implicated in antiviral responses to some DNA viruses.

Recent studies have shown that many common cancers have an inherent reduction in the level of RIP3 protein in the signaling cascade for the programmed cell death pathway known as necroptosis. Mutations in the N-terminus of the E3L protein result in the inability to suppress the necroptosis pathway. Induction of necroptosis results in inhibition of viral replication and spread in cells that retain functional necroptosis pathways. The reduction in RIP3 protein levels that is common in cancer cells makes possible the selective viral replication in cancerous cells and the normal levels of RIP3 protein in non-cancerous cells restricts the spread in healthy cells.

Mutation of the E3L gene from VACV reduced function of the protein's N-terminus and resulted in a virus that was highly debilitated for replication in normal cells (non-cancerous). Referring to FIG. 1, the E3L gene product of the vaccinia virus is a 190 amino acid polypeptide. The E3L gene codes for several functions including a dsRNA-binding protein, a Z-DNA binding protein, and dimerization. Amino acids II 8-190 have been implicated in dsRNA binding. Amino acid numbering as used herein is adopted from Goebel et al., 1990, Virology 179:247-66, 577-63. In some embodiments, a VACV comprises a mutated E3L gene wherein at least one nucleic acid required to encode all 190 amino acids is not present. In other embodiments, a VACV comprises a mutated E3L gene wherein a fragment (VACV-E3LΔ83N) of the E3L gene defined by SEQ ID NO: 1 (ATGGGCCCCATAATAGATGATGTATCCGC-GAAAAATCAATGAGAGAGGATCATAA GTCTTTT-GATGAIGTTATICCGGCTAAAAAAATTATTGATTG-GAAAGGTGCTAACCC TGTCACCGTTATTAATGAGTACTGCCAAATTACTAG-GAGAGATTGGTCTTTTCGTATT GAATCAGTGGGGC-CTAGTAACTCTCCTACATTTTATGCCTGTGTAGA-CATCGACGGA AGAGTATTCGATAAGGCAGATGGAAAATCTAAAC-GAGATGCTAAAAATAATGCAGC TAAATTGGCAGTA-GATAAACTTCTTGGTTACGTCATCATTAGATTCTGA) is not present. In yet other embodiments, a VACVA comprises a mutated E3L gene wherein a fragment of the E3L gene is at least 90% conserved of the sequenced defined by SEQ ID NO: 1 is not present. In yet another embodiment, a VACV comprises a mutated E3L gene wherein a fragment (VACV-E3LΔ54N) of the E3L gene defined by SEQ ID NO: 2 (ATGGTGTACAGCTCCGACGATATTCCTCCTCGT-TGGTTTATGACAACGGAGGCGGAT AAGCCGGAT-GCTGATGCTATGGCTGACGTCATAATAGATGATG-TATCCCGCGAAAA ATCAATGAGAGAGGATCATAAGTCTTTTGATGATGT-TATTCCGGCTAAAAAAATTAT TGATTGGAAAGAT-GCTAACCCTGTCACCATTAATGAGTACTGC-CAAATAACTAA GAGAGATTGGTCTTTTCGTATTGAATCAGTTGGGC-CTAGTAACTCTCCTACATTTTAT GCCTGTGTAGA-CATCGACGGAAGAGTATTCGATAAGGCAGATG-GAAAATCTAAACG AGATGCTAAAAATAATGCAGCTAAATTGGCAGTA-GATAAACTTCTTGGTTACGTCAT CATTAGAT-TCTGA). In yet another embodiment, a VACVA comprises a mutated E3L gene wherein a fragment of the E3L gene is at least 90% conserved of the sequenced defined by SEQ ID NO: 2 is not present.

In certain embodiments, the recombinant vaccinia virus was constructed using homologous recombination, which utilizes transfection with DNA fragments or plasmids containing sequences homologous to viral DNA and infection with wild-type or recombinant vaccinia virus to achieve recombination in infected host cells.

Further, marker rescue techniques were used to identify recombinant vaccinia virus. Representative methods for production of recombinant vaccinia virus by homologous recombination are disclosed by Piecini et al., 1987, Methods in Enzymology 153:545, which is hereby incorporated by reference in its entirety. For example, in certain embodiments, a method for constructing the recombinant vaccinia virus includes a step of infecting host cells with vaccinia virus from which the E3L, gene has been deleted (i.e., a non-naturally occurring, mutated form of vaccinia virus). In some embodiments, the vaccinia virus used as a starting point for preparing the recombinant vaccinia virus of the invention is a naturally occurring strain. In some embodiments, the vaccinia virus used as a starting point for preparing the recombinant vaccinia virus is a non-naturally occurring or engineered strain. In certain embodiment, engineered deletion mutants of Copenhagen strain are used.

In some embodiments, when generating recombination plasmids, the nucleic acid sequences of the vaccinia virus E3L gene and the left and right flanking arms are found in Earl et al., 1993, in Genetic Maps: locus maps of complex genomes, O'Brien, ed., Cold Spring Harbor Laboratory Press, 1. 1 5 7 and Goebel et al., 1990, which is hereby incorporated by reference in its entirety. The amino acid numbering used herein is adopted from Goebel et al., 1990, which is hereby incorporated by reference in its entirety. The vaccinia virus used for recombination may comprise other deletions, inactivations, or exogenous DNA.

In certain embodiments, generation of VACV with E3L N-terminal mutations results in a VACV mutant that (1) allows for selective growth and replication in cancerous cells where RIP3 protein levels are between 0% and about 50% of the protein levels for the given protein expressed in non-cancerous cells of the same type, and (2) does not tend to replicate and spread in healthy (non-cancerous cells) due to the inability to suppress necroptosis. In other words, the cancerous cells have less than normal protein levels of RIP3. Cancerous cells that have less than normal RIP3 protein levels do not undergo necroptosis when infected with specific VACV mutants, thereby allowing the VACV mutants to replicate and kill the cancer cells. These same mutants are severely attenuated in healthy cells, which respond to the infection by induction of necroptosis, preventing the virus from replicating or spreading. In certain embodiments, the VACV mutants are vaccinia viral vectors comprising one or more described E3L gene mutations. As described herein, "about" means a difference of plus or minus 10% in protein expression levels.

The present disclosure presents a method of inducing lysis of cancer cells that are deficient in activating a programmed cell death pathway. In certain embodiments, the method comprises contacting said cancer cells with the VACV mutants. In certain embodiments, VACVs with E3L mutations allow for selective growth and replication in cancerous cells that have less than normal DAI protein levels. The DAI protein levels are also between 0% and about 50% of the protein levels for the given protein expressed in non-cancerous cells of the same type. Further, in certain embodiments, VACVs with E3L mutations allow for selective growth and replication in cancerous cells that have less than normal MLKL protein levels. The MLKL protein levels are also between 0% and about 50% of the protein levels for the given protein expressed in non-cancerous cells of the same type.

Additionally, in certain embodiments, VACVs with E3L mutations allow for selective growth and replication in cancerous cells that have less than normal RIP3 protein levels and DAI protein levels. In other embodiments, VACVs with E3L mutations allow for selective growth and replication in cancerous cells that have less than normal RIP3 protein levels and MLKL protein levels. In yet other embodiments, VACVs with E3L mutations allow for selective growth and replication in cancerous cells that have less than normal DAI protein levels and MLKL protein levels. In yet another embodiment, VACVs with E3L mutations allow for selective growth and replication in cancerous cells that have less than normal RIP3 protein levels, less than normal DAI protein levels, and less than normal MLKL protein levels (or any combination thereof).

The present disclosure further provides a pharmaceutical composition comprising VACV mutants and a method of inducing oncolysis in a subject having a tumor by administering such composition to the subject. Further, the pharmaceutical composition for treating a cancer comprises at least one chemotherapeutic agent and a pharmaceutically acceptable carrier.

Traditional chemotherapeutic agents are cytotoxic, for example, by interfering with cell division (mitosis) but cancer cells vary widely in their susceptibility to these agents. To a large extent, chemotherapy can be thought of as a way to damage or stress cells, which may then lead to cell death if apoptosis is initiated. Many of the side effects of chemotherapy can be traced to damage to normal cells that divide rapidly and are thus sensitive to anti-mitotic drugs: cells in the bone marrow, digestive tract, and hair follicles. This results in the most common side-effects of chemotherapy: myelosuppression (decreased production of blood cells, hence also immunosuppression), mucositis (inflammation of the lining of the digestive tract), and alopecia (hair loss). Because of the effect on immune cells (especially lymphocytes), chemotherapy drugs often find use in a host of diseases that result from harmful overactivity of the immune system against self (so-called autoimmunity). These include Rheumatoid arthritis, Systemic lupus erythematosus, Multiple sclerosis, Vasculitis, and many others.

Such agents can include. (for example, actinomycin, all-trans retinoic acid, azacitidine, azathioprine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, valrubicin, vinblastine, vincristine, vindesine, and vinorelbine). In certain embodiments, this combination therapy attacks both RIP3– and RIP3+ cancer cells. Further, this combination therapy attacks both RIP3– and DAI– cancer cells and RIP3+ and DAI+ cancer cells. The combination therapy can be administered in any known way and with any known pharmaceutically acceptable additives. Moreover, amounts can be based on those used for the chemotherapeutic agents and/or oncolytic vaccinia virus.

The term "carrier" as used herein includes any and all solvents, diluents, dispersion media, antibacterial and antifungal agents, microcapsules, liposomes, cationic lipid carriers, isotonic and absorption delaying agents, and the like. Suitable carriers are known to those of ordinary skill in the art. In certain embodiments, the compositions of the invention can be prepared in liquid forms, lyophilized forms or aerosolized forms. Other optional components, e.g., stabilizers, buffers, preservatives, flavorings, excipients and the like can be added.

The term "administering" includes any route of introducing or delivering to a subject a compound to perform its intended function. A composition comprising a peptide-tetrahedron-drug nanoparticle as provided herein is administered to a subject by any method that achieves the intended purpose or is deemed appropriate by those of skill in the art. For example, a composition of the present invention can be administered as a pharmaceutical, and may be administered systemically or locally via oral or parenteral administration. As used herein, the term "administration" includes oral and parenteral administration. Oral administration includes, for example, administration of oral agents. Such oral agents include, for example, granules, powders, tablets, capsules, solutions, emulsions, and suspensions. Parenteral administration includes, for example, administration of injections. Such injections include, for example, subcutaneous injections, intramuscular injections, intratumoral injection, and intraperitoneal injection. In some cases, intravenous injections such as drip infusions, intramuscular injections, intraperitoneal injections, subcutaneous injections, suppositories, enemas, oral enteric tablets, or the like can be selected.

Appropriate modes of administration can be determined based on the physical location of a tumor or tumors in the subject's body. Compositions can be administered to a subject in need thereof in dosage unit form where each discrete dosage unit contains a predetermined quantity of an active ingredient or compound that was calculated to elicit a desirable therapeutic effect when administered with, in some cases, a pharmaceutically acceptable carrier.

A therapeutically effective dose relates to the amount of a compound which is sufficient to improve the symptoms, for example a treatment, healing, prevention or improvement of such conditions. An "effective amount" of the pharmaceutical composition is defined herein as that amount sufficient to induce oncolysis, the disruption or lysis of a cancer cell, as well as slowing, inhibition or reduction in the growth or size of a tumor and includes the eradication of the tumor in certain instances. An effective amount can also encompass an amount that results in systemic dissemination of the therapeutic virus to tumors indirectly, e.g., infection of non-injected tumors. For dosage determinations, it can be advantageous to assess toxicity and therapeutic efficacy of a compound in cell cultures or in experimental animals. For example, the $LD_{50}$ (i.e., the dose lethal to 50% of the population) and $ED_{50}$ (i.e., the dose therapeutically effective in 50% of the population) can be determined. From these calculations, dosage ranges for use in humans can be formulated. Dosage ranges can vary depending on factors such as mode of administration.

In certain embodiments, oncolysis is induced in more than 90% of cells in tumors. In other embodiments, oncolysis is induced in more than 80% of cells in tumors. In yet other embodiments, oncolysis is induced in more than 70% of cells in tumors.

In certain embodiments, the subject is administered one or more doses of infectious viral particles or plaque forming units (pfu), each dose containing at least $1 \times 10^2$ to $1 \times 10^{10}$ or more infectious viral particles or plaque forming units (pfu), including the various values and ranges therebetween. For example, the subject may be administered one or more doses of between about $1 \times 10^2$ and $1 \times 10^4$, between about $1 \times 10^4$ and $1 \times 10^6$, between about $1 \times 10^6$ and $1 \times 10^8$ or between $1 \times 10^8$ and $1 \times 10^{10}$ pfu of virus.

EXAMPLES

Figure 2A:
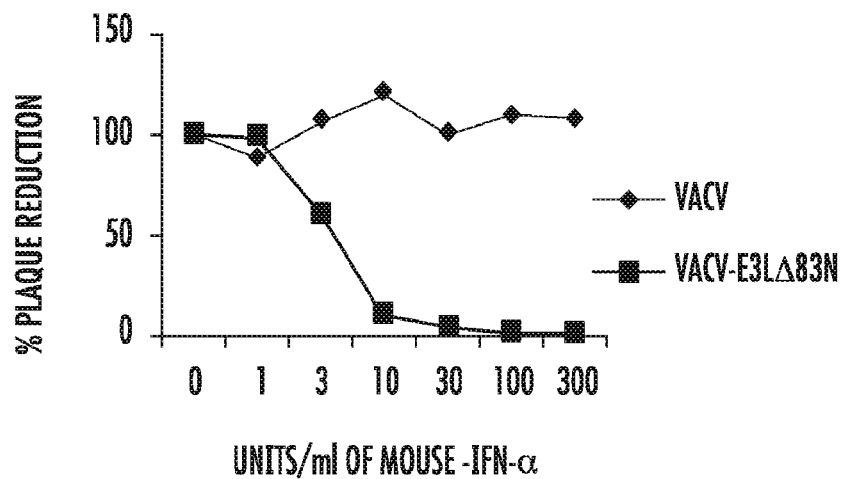

Referring to FIG. 2A, the plaque efficiency, which was measured in plaque-forming unit (PFU)—a measure of the number of particles capable of forming plaques per unit volume—was reduced 50% with mutant vaccinia virus infection compared to with wild type vaccinia virus infection in L929 cells with intact programmed cell death pathways, which were pretreated with type 1 interferon (IFN) between 3 and 10 U/ml for 18 hours. The type of mutant vaccinia viruses used in this exemplary embodiment is an E3 N-terminus truncated mutant (VACV-E3LΔ83N). In other words, the ability of the mutant vaccinia viruses to replicate in L929 cells was severely attenuated compared to wild type vaccinia virus.

Figure 2B:
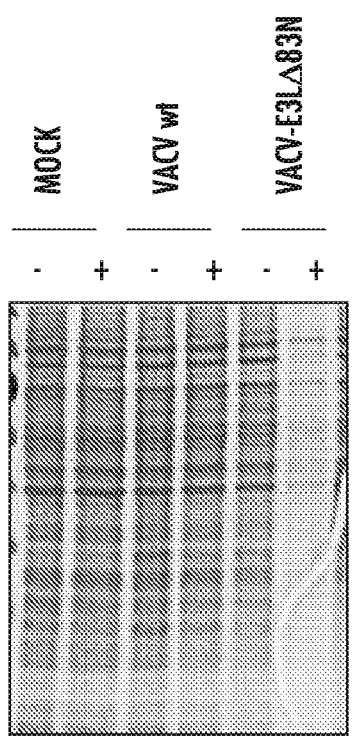
Figure 2D:
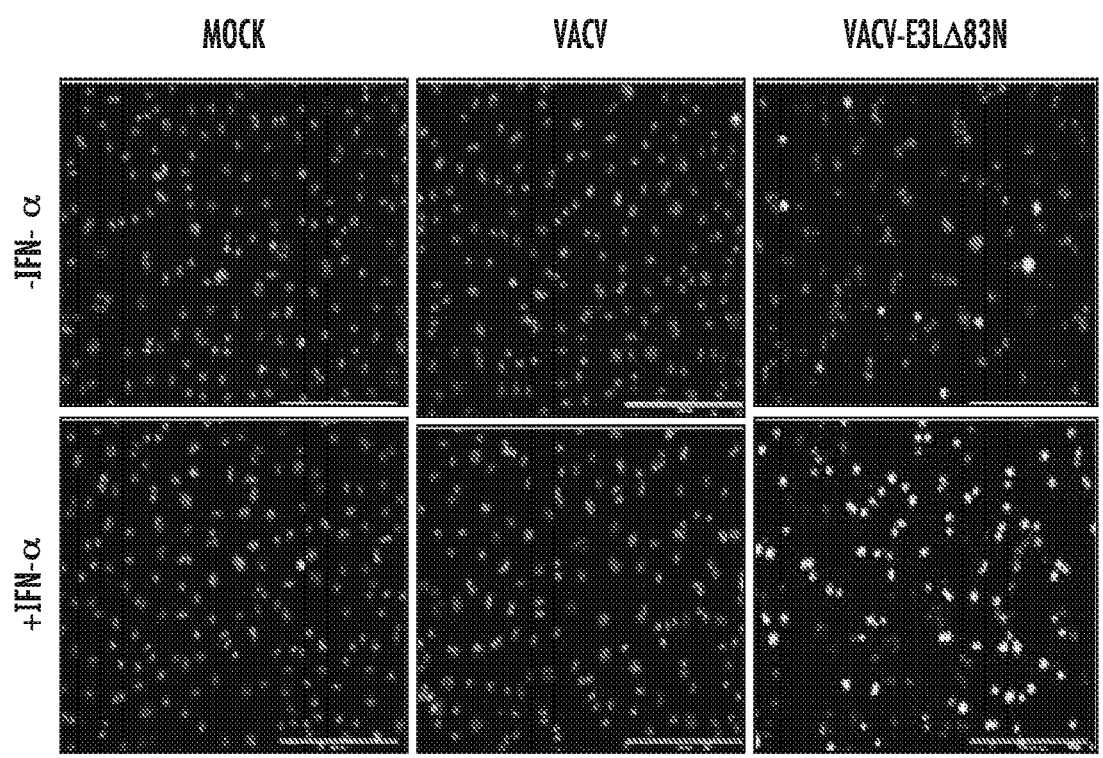

Similarly, comparing L929 cells pretreated with type 1 IFN and subsequently infected with VACV-E3LΔ83N to cells pretreated with type 1 IFN and infected with either wild type vaccinia viruses or mock-infected cells (control, cells are "infected" with only Tris, the virus diluent, and no virus), the live imaging of L929 cells 6 HPI demonstrated a drastic reduction in membrane integrity and morphological changes (FIG. 2C); the Sytox inclusion viability assay showed that L929 cells at 5 HPI have a significant reduction of viability (FIG. 2D); and the commassie blue stained protein gel illustrated a global loss of protein (FIG. 2B). In conclusion, the VACV-E3LΔ83-N-infected L929 cells were able to turn on their programmed cell death pathways and stop the replication of infecting viruses; whereas, the wild type control vaccinia virus was able to evade programmed cell death pathways in infected L929 cells and continued to replicate.

Figure 3A:
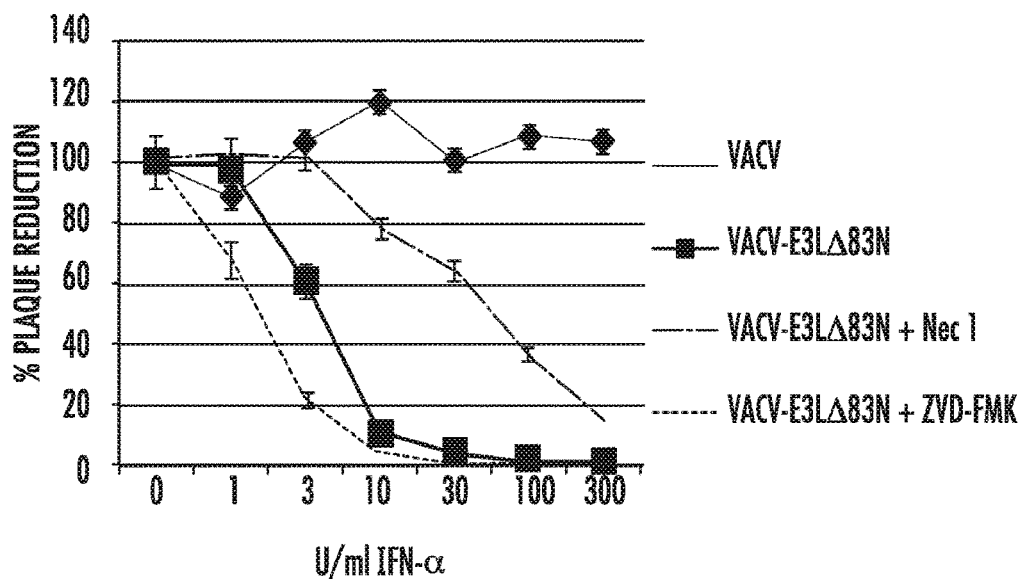
FIGS. 3A-3G: The Z-NA binding domain of VACV E3 functions to inhibit an IFN primed and virally induced necroptosis. (3A) Type-1 IFN induced plaque reduction is inhibited by the treatment of necrostatin-1 which acts on necroptotic proteins but is not inhibited by the pan-caspase inhibitor ZVAD-FMK, which is known to inhibit pyroptosis. (3B) Global protein loss in type-1 IFN treated cells which are subsequently infected with an E3 N-terminus truncated mutant is rescued by an inhibitor of necroptosis. (3C) Loss of membrane integrity and morphological changes in live imaging is inhibited by a necroptosis inhibitor. (3D) Loss of viability demonstrated by Sytox inclusion viability at 5 HPI was rescued by Necrostatin-1. (3E) MLKL aggregation under non-reducing conditions suggests activation of MLKL following induction of necroptosis. (3F) MLKL phosphorylation demonstrated by Western blot indicated that necroptic death is induced as early as 3 HPI. (3G) Cell titer glow cell viability assay confirms that L929 cells pretreated with type-1 IFN and infected with E3 N-terminal mutations undergo necroptosis due to inhibition of death when treated with GSK 872, which is a specific inhibitor of the kinase domain.

Referring to FIG. 3A-3G, the L929 cells infected with wild type vaccinia viruses and VACV-E3LΔ83N were pretreated with type 1 IFN, RIP1 inhibitor necrostatin-1, and pan-caspase inhibitor ZVAD-FMK, which is known to inhibit pyroptosis. Pyroptosis is uniquely dependent on caspase-1, which is not involved in apoptotic cell death and caspase-1 deficient cells respond normally to most apoptotic signals. Referring to FIG. 3A, type 1 IFN-induced plaque reduction in VACV-E3LΔ83N-infected L929 cells was inhibited by the treatment of necrostatin-1, but not by the treatment with pan-caspase inhibitor ZVAD-FMK. This result demonstrates that by inhibiting RIP1 in L929 cells, VACV-E3LΔ83N was able to evade the necroptotic pathways and form plaques. Further, pyroptotic pathway inhibition did not affect the ability of VACV-E3LΔ83N to form plaques.

Figure 3B:
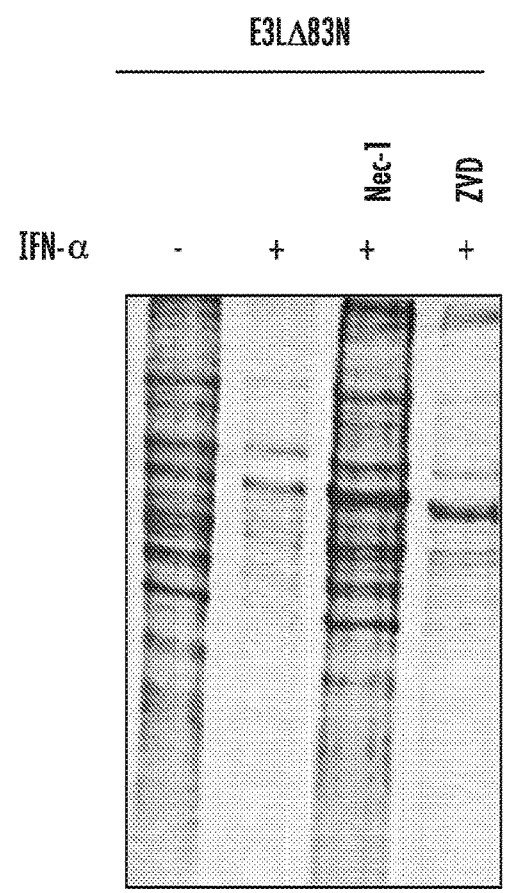
Figure 3C:
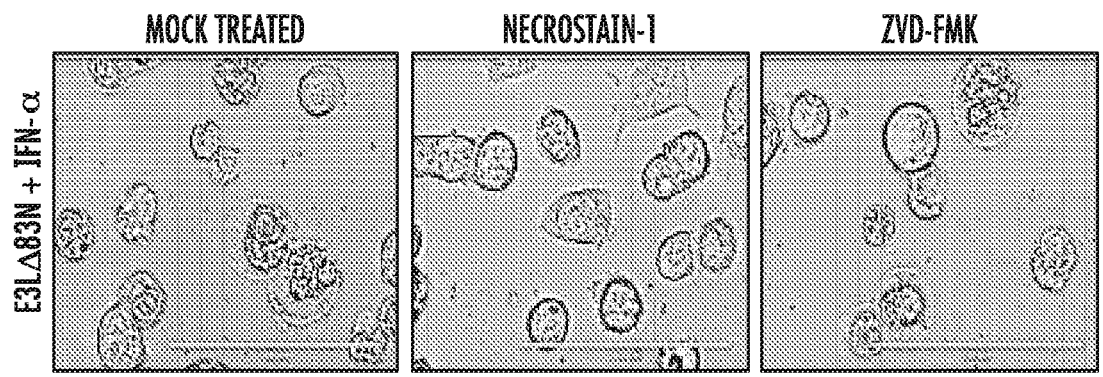
Figure 3D:
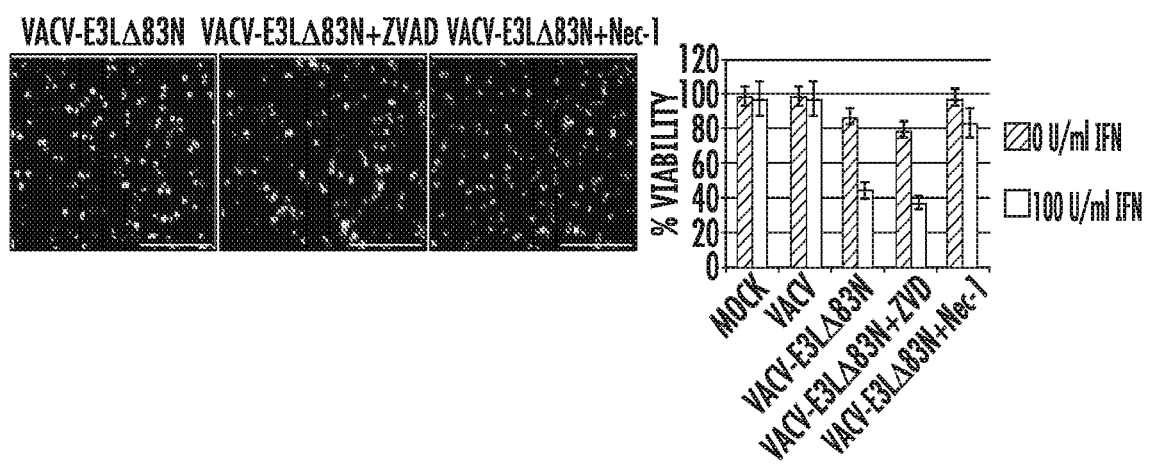
Figure 3E:
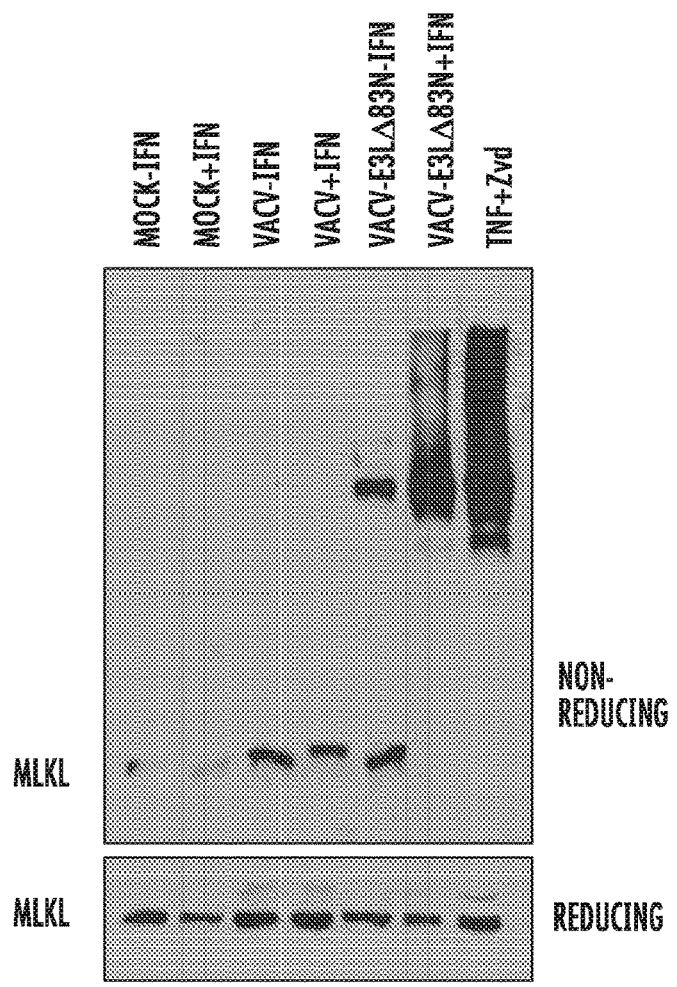
Figure 3F:
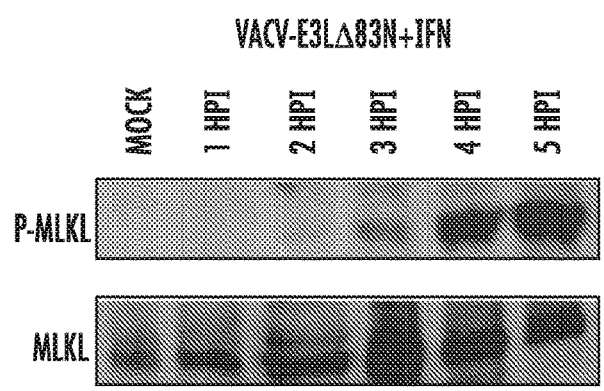
Figure 3G:
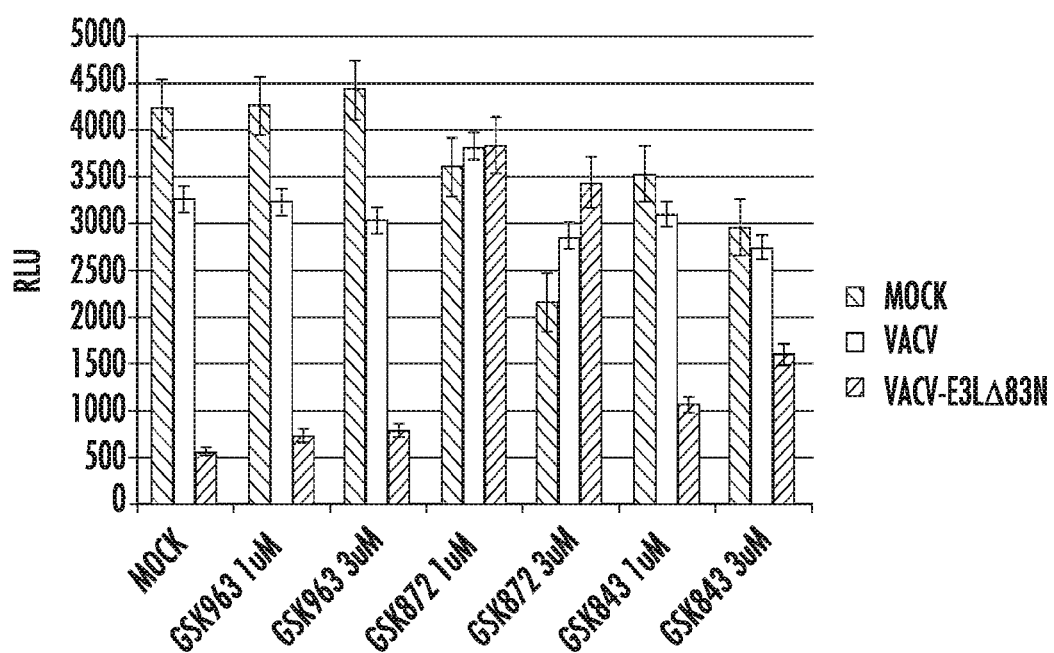

Referring to FIG. 3B, the commassie blue stained protein gel illustrates a global loss of protein in VACV-E3LΔ83N-infected cells is rescued by treatment with necrostatin-1. Further, referring to FIG. 3C, the live imaging of L929 cells 6 HPI demonstrated that a drastic reduction in membrane integrity and morphological changes in VACV-E3LΔ83N-infected cells is rescued by treatment with necrostatin-1. Moreover, referring to FIG. 3D, the Sytox inclusion viability assay showed that a significant reduction of viability in VACV-E3LΔ83N-infected L929 cells at 5 HPI is rescued by the treatment with necrostatin-1.

Figure 4A:
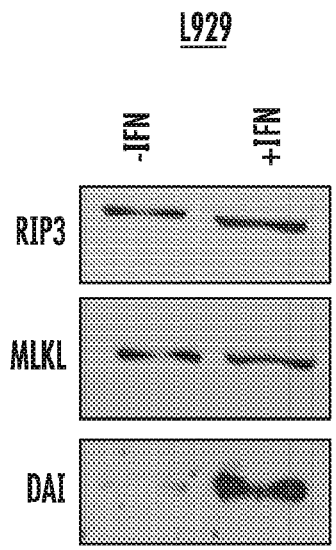
FIGS. 4A-4D: IFN primed necroptosis is responsible for the attenuation of E3 N-terminal mutations and is dependent on both RIP3 and DAI (ZBP-1). (4A) Western blot demonstrating that DAI is up-regulated by type-1 IFN treatment. (4B) qPCR indicating that other necroptosis proteins are not up-regulated by pre-treatment of type-1 IFN in L929 cells. (4C) Virally induced death is rescued in non-necroptosis sensitive HEK293T cells co-transfected with both RIP3 and DAI but not RIP3 alone, indicating the requirement of both proteins in VACV-induced necroptosis. (4D) Pathogenesis of E3 N-terminal mutants is rescued in both RIP3−/− mice and ZBP-1−/− (DAI−/−) mice.
Figure 4B:
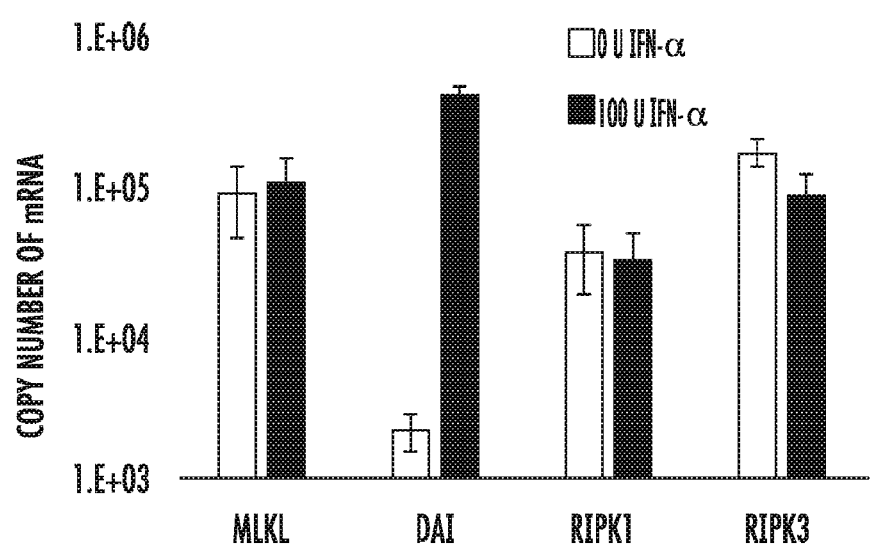
Figure 4C:
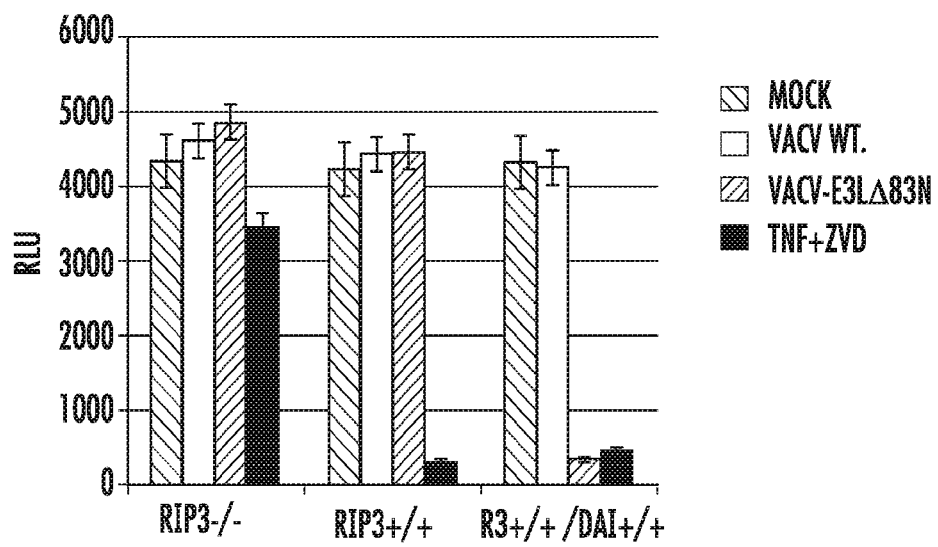
Figure 4D:
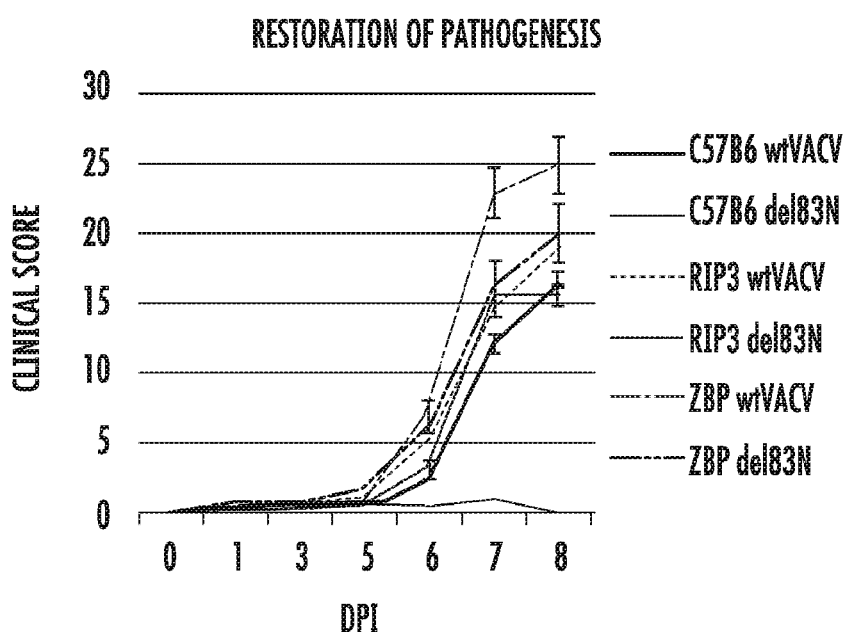

Now referring to FIGS. 4A and 4B, DAI is upregulated by IFN treatment, which induces necroptosis in cells. Further, FIG. 4C demonstrated in this example that normal expression or upregulation of both RIP3 and DAI levels were required to induce plaque reduction and reduce cell viability in VACV-E3LΔ83N-infected cells after IFN treatment. Moreover FIG. 4D demonstrates that in RIP3-/- mice or DAI-/- mice, VACV-E3LΔ83N- was able to evade the necroptotic pathway and cause disease in the animals. The following symptoms were assigned a value to determine a clinical score: weight loss, sneezing, ruffled coat, lethargy or slow movement, labored breathing, and ocular infections.

Based on the above demonstration, the mutant vaccinia viruses in the present disclosure are able to selectively reproduce in RIP3-deficient, DAI-deficient, or RIP3- and DAI-deficient cells to evade the necroptotic pathway, replicate, and eventually lead to host cell lysis. Many cancerous tumors possess mutations in one or more of the cellular anti-viral signaling pathways that modify cellular growth; N-terminal mutations in a VACV essential immune-evasion protein (the product of the E3L gene) can render VACV dependent on dysregulated anti-viral signaling pathways for replication, thus allowing for selective lysis of the cancerous cells and leaving healthy cells unaffected.

Figure 5A:
FIGS. 5A-5D: 4T1 syngeneic tumors were induced in each hind flank of BALB/c mice. (5A) The right side tumors only were treated three times with either PBS or with $1 \times 10^7$ pfu of VACV-E3LΔ54N. (5B) The images were taken three weeks post-treatment. Additionally, tissue was harvested from both syngeneic and xenograft tumors and sections were stained for VACV. (5C) Where the treatment was PBS (no virus), there is no brown precipitate visible in the injected tumor (top panel). The bottom right panel shows the virus presence, as expected, in the injected tumor. However, the same virus presence can be seen in the bottom left panel, showing the uninjected left tumor. (5D) The bottom panels indicate the presence of virus in the left side tumors uninjected). In both types of tumors, syngeneic and xenograft, the virus spread to the uninjected left side tumor from the injected right side tumor.
Figure 5B:
Figure 5C:
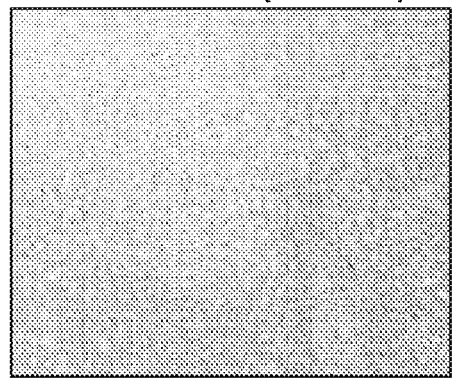
Figure 5C:
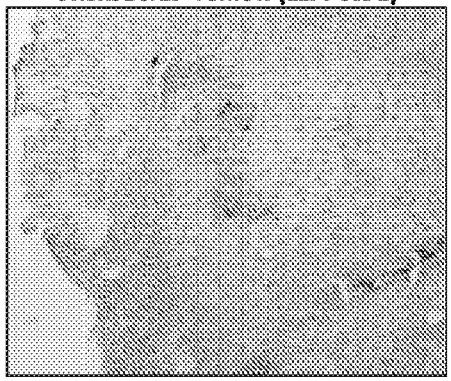
Figure 5C:
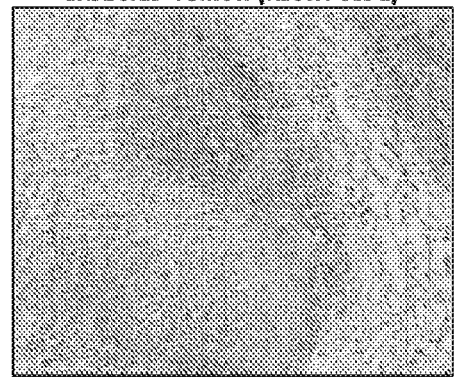
Figure 5D:
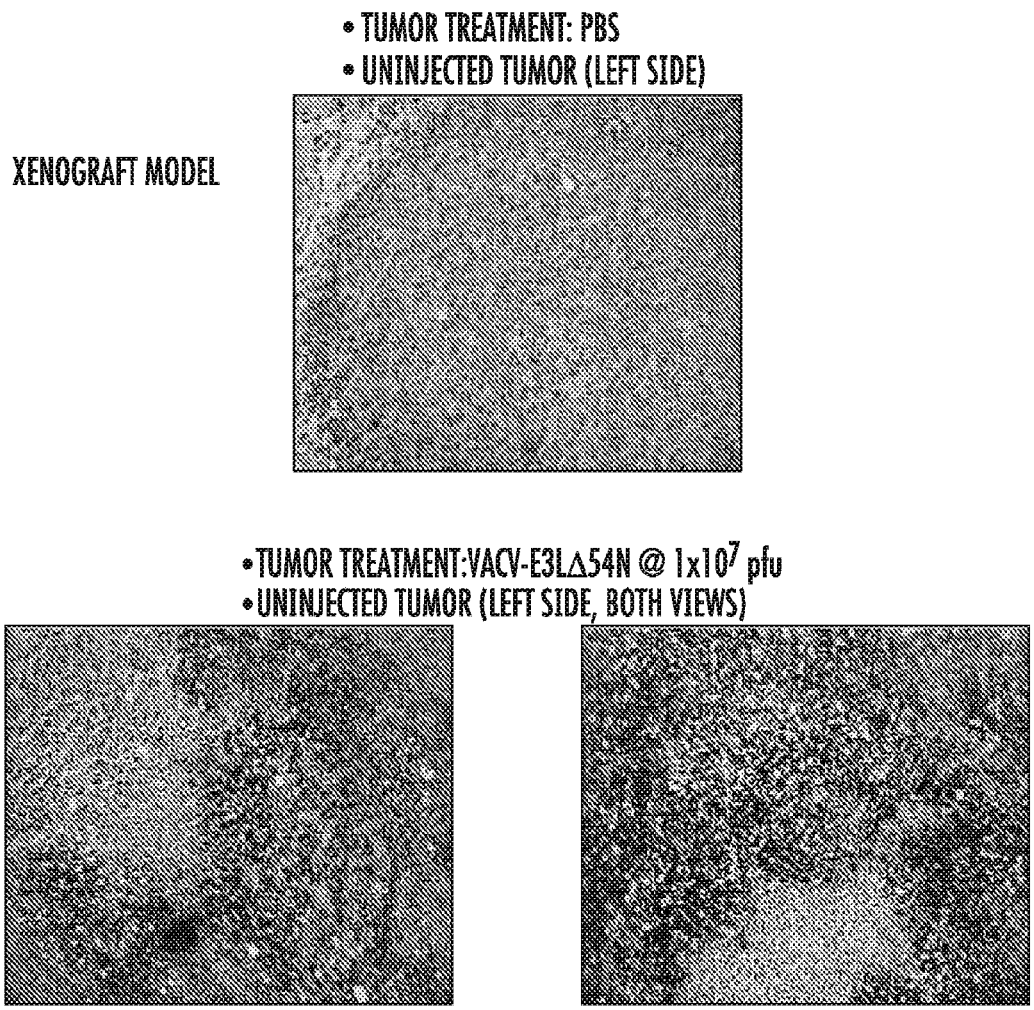

VACV-E3L N-terminal mutants were capable of spreading from the treated tumors to the untreated tumors in both a xenograph and a syngenetic mouse model. Referring to FIGS. 5A-5B, 4T1 syngeneic tumors were induced in each hind flank of BALB/c mice. The right side tumors only were treated three times with either PBS (A) or with $1 \times 10^7$ pfu of VACV/-E3LΔ54N (B). The images were taken three weeks post-treatment. Additionally, tissue was harvested from both syngeneic and xenograft tumors and sections were stained for VACV (indicated by brown precipitate). In FIG. 5C, where the treatment was PBS (no virus), there is no brown precipitate visible in the injected tumor (top panel). The bottom right panel shows the virus presence, as expected, in the injected tumor. However, the same virus presence can be seen in the bottom left panel, showing the uninjected left tumor. Similarly, in FIG. 5D, the bottom panels indicate the presence of virus in the left side tumors (uninjected). In both types of tumors, syngeneic and xenograft, the virus spread to the uninjected left side tumor from the injected right side tumor. These data suggested that VACV-E3L N-terminal mutants could be effective oncolytic viruses for the treatment of cancer.

Figure 6A:
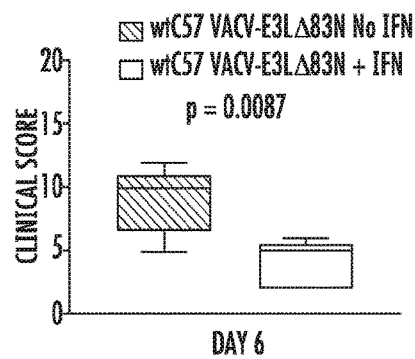
FIGS. 6A and 6B: Loss of MLKL (the executioner for the necroptosis pathway) rescues replication of VACV-E3LΔ83N in Interferon-treated mice. (A) Wild type C57 mice were infected with VACV-E3LΔ83N, either treated or not treated with interferon, and monitored daily for clinical symptoms of disease. Interferon induces the necroptotic pathway, killing the virus and reducing clinical symptoms in the treated mice compared to mice not treated with interferon. (B) Transgenic C57 mice with the MLKL gene knocked out were infected with VACV-E3LΔ83N, either treated or not treated with interferon, and monitored daily for clinical symptoms of disease. In the absence of MLKL, there is no necroptosis; the virus is able to replicate and cause disease even in the presence of interferon treatment.
Figure 6B:
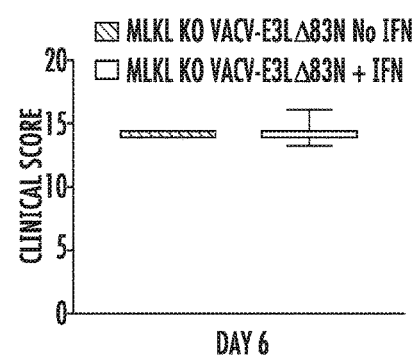

Referring to FIGS. 6A and 6B, wild type C57 mice were infected with VACV-E3LΔ83N, either treated or not treated with interferon, and monitored daily for clinical symptoms of disease. Interferon induces the necroptotic pathway, killing the virus and reducing clinical symptoms in the treated mice compared to mice not treated with interferon. (B) Transgenic C57 mice with the MLKL gene knocked out were infected with VACV-E3LΔ83N, either treated or not treated with interferon, and monitored daily for clinical symptoms of disease. In the absence of MLKL, there is no necroptosis; the virus is able to replicate and cause disease even in the presence of interferon treatment.

Figure 7:
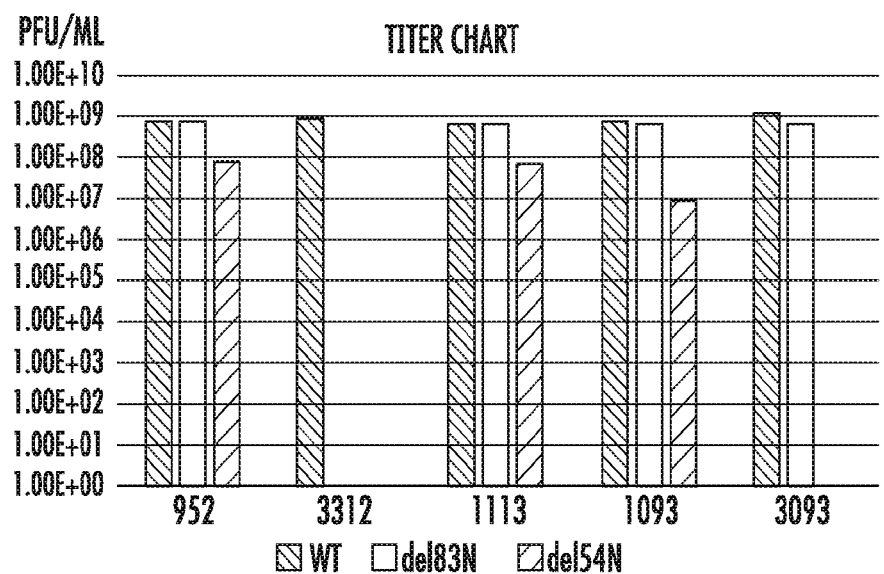
FIG. 7: Melanoma cell lines screened for replication of viruses expressing a modified N-terminus of the E3 protein. Melanoma cell lines were screened to identify those that will support replication of VACV-E3LΔ54N and VACV-E3LΔ83N. Cell lines 952, 1113, and 1093 support replication of both mutant viruses, while 3093 is permissive for VACV-E3LΔ83N only. Replication of the mutant viruses indicates that the necroptotic pathway is disabled in these melanoma cell lines, and therefore these lines are good candidates for testing virus-induced regression of tumors in mice. These four cell lines will be used to inoculate the flank tissue of mice; following visible tumor growth, the tumors will be treated with one of the two viruses and monitored for regression, We hypothesize that in the absence of necroptosis, the virus will replicate in the cancer cells, resulting in tumor regression. In normal (non-cancerous) cells, the necroptosis pathway is intact, and the virus will not spread among normal cells.

Referring to FIG. 7, Melanoma cell lines were screened to identify those that will support replication of VACV-E3LΔ54N and VACV-E3LΔ83N. Cell lines 952, 1113, and 1093 support replication of both mutant viruses, while 3093 is permissive for VACV-E3LΔ83N only. Replication of the mutant viruses indicates that the necroptotic pathway is disabled in these melanoma cell lines, and therefore these lines are good candidates for testing virus-induced regression of tumors in mice. These four cell lines will be used to inoculate the flank tissue of mice; following visible tumor growth, the tumors will be treated with one of the two viruses and monitored for regression. We hypothesize that in the absence of necroptosis, the virus will replicate in the cancer cells, resulting in tumor regression. In normal (non-cancerous) cells, the necroptosis pathway is intact, and the virus will not spread among normal cells.

Mice are inoculated with the melanoma cells lines 952, 1113, 1093, or 3093. After the tumor growth in each group of mice inoculated with one of the aforementioned melanoma cell lines, the disclosed composition comprising VACV-E3LΔ83-N is directly injected into the tumor. Subsequent regression of the injected tumor and non-injected tumor is monitored and studied.

While exemplary embodiments of the present invention have been described and illustrated in detail, it should be apparent to those of ordinary skill in the art that modification and adaptations to those embodiments may occur without departing from the scope of the present invention.

We claim:

1. A method of inducing lysis of cancer cells of a subject that have a deficiency in an ability to activate a programmed cell death pathway, comprising
    screening cancer cells of the subject for expression of at least one of receptor-interacting protein kinase (RIP) 3, DNA-dependent activator of interferon regulatory factor (DAI), and mixed lineage kinase domain-like protein (MLKL);

selecting the subject for treatment if the screened cancer cells have between about 0% to about 50% of expressed protein levels, in comparison to non-cancerous cells of the same type, of at least one of RIP3, DAI, and MLKL; and contacting cancer cells of the selected subject with a vaccinia virus (VACV) having an inactivating mutation in an E3L gene of said virus, thereby inducing lysis of the contacted cancer cells.

2. The method of claim 1, wherein said cancer cells have between about 0% to about 50% of expressed protein levels, in comparison to non-cancerous cells of the same type, of both RIP3 and DAI.

3. The method of claim 1, wherein said cancer cells have between about 0% to about 50% of expressed protein levels, in comparison to non-cancerous cells of the same type, of both RIP3 and MLKL.

4. The method of claim 1, wherein the E3L gene of said virus is SEQ ID NO: 1.

5. The method of claim 1, wherein the E3L gene is at least 90% identical with the sequence represented by SEQ ID NO: 1.

6. The method of claim 1, wherein the VACV has a mutation in the E3L gene of said virus represented by deleting the entire E3L gene.

7. A method of inducing oncolysis in a subject having a tumor comprising cancer cells that have a deficiency in an ability to activate a programmed cell death pathway, comprising screening cancer cells of a tumor of the subject for expression of at least one of receptor- interacting protein kinase (RIP) 3, DNA-dependent activator of interferon regulatory factor (DAI), and mixed lineage kinase domain-like protein (MLKL);

selecting the subject for treatment if the screened cancer cells of the tumor have between about 0% to about 50% of expressed protein levels, in comparison to non-cancerous cells of the same type, of at least one of RIP3, DAI, and MLKL; and administering to the selected subject a therapeutic effective amount of a pharmaceutical composition comprising a vaccinia virus (VACV) having an inactivating mutation in an E3L gene of said virus, whereby administration results in lysis of cancer cells of the tumor.

8. The method of claim 7, wherein said cancer cells have between about 0% to about 50% of normal cell expression levels of both RIP3 and DAI.

9. The method of claim 7, wherein said cancer cells have between about 0% to about 50% of normal cell expression levels of both RIP3 and MLKL.

10. The method of claim 7, wherein the administering further comprises injection into the tumor, whereby oncolysis is induced in the tumor and in at least one tumor that is not injected with the VACV.

11. The method of claim 7, wherein the tumor is a melanoma tumor, a breast tumor, or a colon tumor.

12. The method of claim 7, further comprising administering to the subject a therapeutic effective amount of at least one chemotherapeutic agent.

* * * * *